(12) United States Patent
Prevost

(10) Patent No.: US 9,090,029 B2
(45) Date of Patent: Jul. 28, 2015

(54) PULTRUSION PROCESS FOR PREPARING COMPOSITES HAVING LOW PERCENTAGE OF FIBERS AND ARTICLES MADE FROM SAME

(75) Inventor: Julien J. Prevost, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 254 days.

(21) Appl. No.: 13/366,980

(22) Filed: Feb. 6, 2012

(65) Prior Publication Data

US 2013/0204368 A1  Aug. 8, 2013

(51) Int. Cl.
*B29C 70/52* (2006.01)
*B29C 70/50* (2006.01)
*A61F 2/30* (2006.01)
*A61L 27/44* (2006.01)
*A61F 2/44* (2006.01)

(52) U.S. Cl.
CPC ........... *B29C 70/506* (2013.01); *A61F 2/30965* (2013.01); *A61L 27/44* (2013.01); *B29C 70/523* (2013.01); *A61F 2/4455* (2013.01); *A61F 2002/3093* (2013.01); *A61F 2002/4495* (2013.01); *A61F 2310/00017* (2013.01); *A61F 2310/00023* (2013.01); *A61F 2310/00029* (2013.01); *A61F 2310/0097* (2013.01); *A61F 2310/00161* (2013.01); *A61F 2310/00179* (2013.01); *A61F 2310/00293* (2013.01); *A61F 2310/00329* (2013.01); *A61F 2310/00976* (2013.01); *A61L 2430/38* (2013.01)

(58) Field of Classification Search
CPC .... B29C 70/52; B29C 70/521; B29C 70/506; B29C 70/523
USPC .................................................. 264/136, 137
See application file for complete search history.

(56) References Cited

U.S. PATENT DOCUMENTS

| | | | | |
|---|---|---|---|---|
| 3,041,673 A * | 7/1962 | Goodwine | .................... | 264/313 |
| 3,466,210 A * | 9/1969 | Wareham | ........................ | 156/86 |
| 3,848,406 A * | 11/1974 | Tabei et al. | ..................... | 57/229 |
| 4,211,818 A * | 7/1980 | Ackley | .......................... | 428/367 |
| 4,265,981 A * | 5/1981 | Campbell | ..................... | 428/591 |
| 4,559,862 A * | 12/1985 | Case et al. | ......................... | 87/1 |
| 4,567,917 A * | 2/1986 | Millard | ........................ | 138/126 |
| 4,741,873 A * | 5/1988 | Fischer et al. | ................ | 264/103 |
| 4,976,812 A * | 12/1990 | McConnell et al. | .......... | 156/148 |
| 5,001,961 A * | 3/1991 | Spain | ................................ | 87/1 |
| 5,080,547 A * | 1/1992 | Moghe | ........................... | 411/436 |
| 5,633,074 A * | 5/1997 | Muroi et al. | ................... | 428/213 |
| 5,674,286 A * | 10/1997 | D'Alessio et al. | ............ | 424/423 |
| 6,184,161 B1* | 2/2001 | Verpoest | ....................... | 442/199 |
| 2004/0106726 A1* | 6/2004 | Joshi et al. | .................... | 524/589 |
| 2011/0106162 A1* | 5/2011 | Ballard et al. | ................ | 606/254 |
| 2011/0129350 A1* | 6/2011 | Grove-Nielsen et al. | ..... | 416/230 |

* cited by examiner

*Primary Examiner* — Matthew Daniels

(57) ABSTRACT

An improved pultrusion process for preparing composite materials having about 10 percent to about 45 percent by volume of reinforcing fibers so as to produce a composite material having enhanced flexibility as compared with composite materials having a higher percent of reinforcing fibers by volume. Articles of manufacture made from composite material produced by the improved pultrusion process, specifically spinal implants, are also provided.

19 Claims, 1 Drawing Sheet

PULTRUSION PROCESS FOR PREPARING COMPOSITES HAVING LOW PERCENTAGE OF FIBERS AND ARTICLES MADE FROM SAME

TECHNICAL FIELD

The present disclosure generally relates to processes for forming low percentage fiber reinforced polymer matrices. More particularly, this disclosure relates to composite structures formed by a pultrusion process in which reinforcing fibrous material is braided with a material having a lower melting point than the continuous fibrous material that melts as it passes through a heated die to produce a composite having a low percentage of continuous fibers.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes discectomy, laminectomy, fusion and implantable prosthetics. As part of these surgical treatments, spinal implants are used. These implants must be made from biocompatible material having high tensile strength and various degrees of flexibility. One suitable material that can be used to produce these implants is thermoplastic composite material manufactured using a pultrusion process.

The pultrusion process as commonly practiced uses reinforcing material, for example, glass filaments, or other reinforcing fibers such as carbon and high strength organic fibers, combined in associated groupings or "tows" that are passed through a tank containing the polymer which is to form the continuous phase in the form of a liquid solution, or in melted form. The plastic coated tows are thereafter drawn through a heated die. The coated tows emerging from the heated die as a relatively rigid composite having reinforced fibers positioned throughout the material. In order to be able to pull the composite through the heated curing die there must be a relatively high percentage of reinforcing fibers in the composite. However, a composite material produced having a relatively high percentage of continuous reinforcing fibers results in a less flexible composite material than materials having a lower concentration of continuous fibers.

Accordingly, the thermoplastic composite material produced by existing pultrusion processes are often too rigid to be suitable for the manufacture of biological implants, for example spinal implants, because of the high percentage of continuous fibers required to support the existing pultrusion process make the material very rigid. This disclosure describes an improved pultrusion process and articles manufactured therefrom that has a lower fiber content and is more flexible than existing pultrusion products.

SUMMARY OF THE INVENTION

Accordingly, a pultrusion process for preparing a fiber reinforced composite material having a low percentage of continuous fibers is disclosed for manufacturing articles, such as implants, having more flexibility than articles made from pultrusion composite materials having a higher percentage of reinforced fibers.

In one particular embodiment, in accordance with the principles of the present disclosure, a pultrusion process for preparing a composite rod having a low percent of continuous reinforcing fibers by volume is provided. The process comprises the steps of providing continuous reinforcing fibers wrapped and/or braided with strands of matrix material having a lower melting point than a melting point of the continuous reinforcing fibers. These wrapped/braided continuous reinforcing fibers are then directed through a heated curing die that melts the matrix material wrapped about the reinforcing fibers so as to produce a solid fiber reinforced composite. As the composite material is feed into the heated die, the next step includes withdrawing the solid fiber reinforced composite from the heated curing die after it is cured. The resulting solid fiber reinforced composite material, for example a thermoplastic material reinforced with glass continuous fibers, has a percentage of continuous fibers in the solid between about 10% to about 45% by volume. The wrapped/braided fibers provide sufficient strength to allow the composite to be withdrawn from the heated die while the resulting composite rod has a lower percentage of reinforcing fibers than a composite rod produced by existing pultrusion methods.

In another embodiment, in accordance with the principles of the present disclosure, an article manufactured from a solid fiber reinforced composite having a low percentage of reinforced fibers are produced. The pultrusion process according to the present disclosure comprises continuously pulling reinforcing fibers through an impregnation chamber comprising a mixture containing precursors and initiators that polymerize when heated above a reaction temperature to produce impregnated continuous reinforcing fibers is provided. Once produced, the impregnated continuous reinforcing fibers are wrapped and/or braided with strands of matrix material having a lower melting point than a melting point of the continuous reinforcing fibers to produce wrapped impregnated continuous reinforced fibers. Once wrapped, the wrapped impregnated continuous reinforcing fibers are directed through a heated curing die to melt the matrix material about the reinforcing fibers so as to produce a solid fiber reinforced composite. The solid fiber is withdrawn from the heated curing die and has a low percentage of continuous fibers in the solid fiber reinforced composite, for example, between about 10% to about 45% by volume. The solid composite is then machined into an article, for example, such as a medical implant, that has increased flexibility as compared to implants made from existing pultrusion processes where a higher percentage of reinforcing fibers are used.

In one embodiment, in accordance with the principles of the present disclosure, the article manufactured from a solid fiber reinforced composite produced from the pultrusion process according to present disclosure is a spinal implant, such as a rod or plate.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
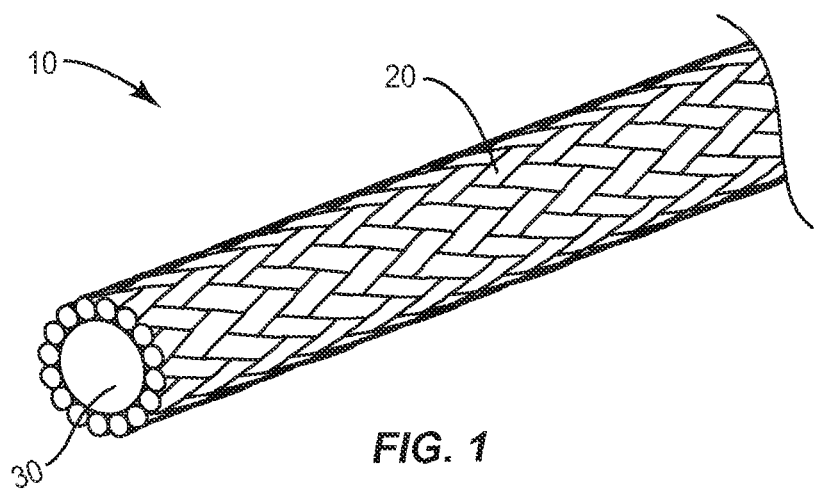
FIG. 1 is a side view of a wrapped or braided reinforcing fibers, of one particular embodiment of a bone fastener in accordance with the principles of the present disclosure.

The present disclosure provides a pultrusion process for producing fiber-reinforced thermoplastic or thermoset composite material having about 10% to about 45% by volume of reinforced fibers that has increased flexibility over composite material made according to existing standard pultrusion methods having much higher percentage by volume of reinforcing fibers.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The composite material of the present disclosure is prepared using a pultrusion method discussed herein that generally wraps and/or braids individual reinforcing fibers, for example such as glass or wire fibers, with fibrous material having a lower melting point than the melting point of the reinforcing fibers. In one embodiment of the present disclosure, individual reinforcing fibers or bundles of reinforcing fibers are first impregnated with a resin, for example a polymeric material such as polyester. The impregnated reinforcing fibers are then wrapped or braided with fibrous material having a lower melting point than the melting point of the reinforcing fibers, so as to provide additional bulk and strength to the reinforcing fibers. The additional bulk and strength of the wrapped and/or braided reinforcing fibers allows a reduced amount of reinforcing fibers to be used in the pultrusion process in order to pull the material through the heated die. That is, since the reinforcing fibers are wrapped and/or braided with fibrous material going into the heated die they have additional strength and therefore less of the continuous fibers are required to pull the pultrusion material through the heated die as it is being cured.

It is envisioned that the pultrusion process of the present disclosure may be used to manufacture implants, for example plates, rods or vertebral implants that can be employed to treat spinal disorders such as, for example, degenerative disc disease, disc herniation, osteoporosis, spondylolisthesis, stenosis, scoliosis and other curvature abnormalities, kyphosis, tumor and fractures. It is further envisioned that the implants manufactured using the pultrusion technique described in the present disclosure may be employed with surgical treatments including open surgery and minimally invasive procedures, of such disorders, such as, for example, discectomy, laminectomy, fusion, bone graft, implantable prosthetics and/or dynamic stabilization applications. It is further contemplated that the disclosed pultrusion process can be used to make a solid composite pultrusion materials having predetermined properties, for example, strength and flexibility, that can be used to manufacture bone fasteners, rods, plates and other implants that may be employed in a surgical treatment with a patient in a prone or supine position, employing a posterior, lateral or anterior approach. The implants made from the composite material produced according to the disclosed pultrusion process may be employed with procedures for treating the lumbar, cervical, thoracic and pelvic regions of a spinal column.

Implants prepared from materials produced according to the pultrusion process described herein generally have fewer reinforcing fibers, for example between about 10% to about 45% by volume, than implants prepared from other pultrusion techniques.

Figure 2:
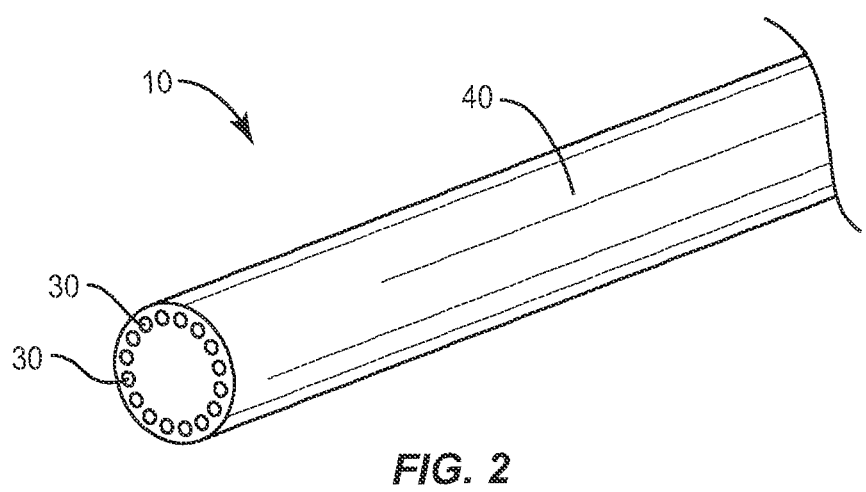
FIG. 2 is a cross-sectional view of a solid composite pultruded rod produced in accordance with the principles of the present disclosure wherein the reinforced fibers are on the periphery.
Figure 3:
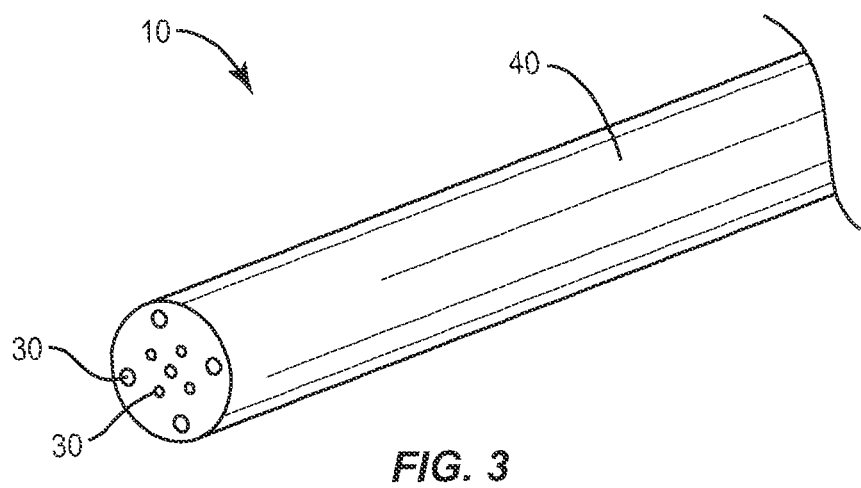
FIG. 3 is a side view of a solid composite pultruded rod produced in accordance with the principles of the present disclosure wherein the reinforced fibers are concentrated in the center.

The following discussion includes a description of a pultrusion process, resulting composite material, and implants made from the composite materials, such as rods, plates and bone fasteners related components and exemplary methods of employing the implants in accordance with the principles of the present disclosure. Alternate embodiments are also disclosed. Reference will now be made in detail to the exemplary embodiments of the present disclosure, which are illustrated in the accompanying figures. Turning now to FIGS. 1-3, there is illustrated components used in the pultrusion process, composite material configurations, and implants in accordance with the principles of the present disclosure.

In one embodiment, in accordance with the principles of the present disclosure, the pultrusion method provides individual reinforcing fibers or bundles of reinforcing fibers impregnated with a resin, for example a polymeric material such as polyester. As shown in FIGS. 1-3, impregnated or non-impregnated reinforcing fibers 30 are wrapped and/or braided with fibers 20 produced from thermoset or thermoplastic materials having a lower melting point that the continuous reinforcing fiber 30 so as to provide a wrapped and/or braided continuous fiber 10 having additional bulk and strength. The additional bulk and strength of the wrapped and/or braided reinforcing fibers 10 allows for a reduced number or volume of reinforcing fibers to be used in the pultrusion composition but, yet still provides the required strength to pull the pultrusion material through the heated die in order to produce a cured composite material. The resulting cured material has between about 10% to about 45% reinforcing fibers by volume. In another embodiment of the present disclosure, the resulting cured material has between about 15% to about 40% by volume. In yet another embodiment of the present disclosure, the resulting cured material has between about 25% to about 35% by volume. The degree of flexibility of the resulting composite material is inversely proportional to the amount of continuous reinforcing fibers in the resulting composite. That is, the more reinforcing fibers in the final composite, the less flexibility the resulting composite material and the implants made from the material will have.

The flexibility of the resulting composite material can also be controlled by the placement or positioning of the reinforced fibers in the composite material. Since the resulting composite material has a lower percentage of reinforced fibers, these fibers can be arranged in such a way as to produce a predetermined desired flexibility. That is, as shown in FIGS. 2 and 3, the reinforcing fibers can be placed around the periphery of the resulting composite material to provide a structure having a less flexible outer surface than inner core. Alternatively, the reinforcing fibers can be arranged in the center of the composite material so as to make the resulting composite material more flexible around the edges than in the center. Still further, the composite material can also have the reinforcing fibers evenly dispersed throughout the resulting composite so as to provide a composite having uniformed flexibility and strength. It is envisioned that various other arrangements can be used so as to produce composite materials having different desired flexibility and strength. A particular composite material can be produced or selected to make an implants having a desired flexibility profile.

The resulting implant produced from the selected composite material can be further machined to provide the final configuration of the implant. For example, once a rough implant is machined from the composite material produced according to the disclosed disclosure, textured surfaces, chamfer surfaces, cavities and openings can be machined into the implant in order to produce the final product. The amount of flexibility of a particular implant can be controlled by the number of reinforcing fibers, the amount of braiding, as well as, the type of thermoplastic or thermoset used in the pultrusion process. As stated above, implants prepared from composite material produced according to the pultrusion method disclosed herein generally have fewer reinforcing fibers, for example between about 10% to about 45% by volume. These fibers can be orientated in the same direction, at an angle or in a predetermined orientation in order to produce a composite having the desired properties. That is, the reinforcing fibers can be arranged in a direction and/or orientated so that they are substantially parallel to the longitudinal axis, substantially perpendicular to the longitudinal axis, oblique to the longitudinal axis or some combination thereof. Each orientation provides different degrees of flexibility. For example, as stated above, an implant made form composite material where all of the reinforced fibers are positioned around the perimeter of the solid composite has a more flexible inner portion than outer portion.

In yet another embodiment of the pultrusion process in accordance with the present disclosure is prepared using chopped reinforced fibers, fragmented reinforced plates, or particulates of the reinforced elements in addition to the continuous reinforcing fibers discussed above. These fragments can be coated on the material used to braid the reinforcing fibers so as to provide continuous fibers and short fragments and/or plates within the resulting composite material. This adds additional strength to the resulting composite material without significantly changing flexibility of the resulting composite material. Since the fragments of the reinforced fibers are not continuous, they move autonomously to one another and therefore do not significantly change the flexibility of the resulting composite material. The reinforced material these fragments/plates can be cured in accordance with the process of the present disclosure as discussed above.

The reinforcing fibers of the present disclosure can be made form one or more of the following materials suitable for medical applications, including metal wires, polymers, ceramics, biocompatible materials and/or their composites, depending on the particular application and/or preference of a medical practitioner. For example, reinforcing fibers can be fabricated from materials such as commercially pure titanium, titanium alloys, Grade 5 titanium, cobalt-chrome alloys, stainless steel alloys, metallic alloys, glass, carbon fibers, as well as man-made products that have a higher melting point than the matrix in which they wrapped/braided with according to the principle of the disclosed pultrusion process.

Materials used to wrap or braid the reinforcing fibers include but are not limited to thermoplastics such as polyaryletherketone (PAEK) including polyetheretherketone (PEEK), polyetherketoneketone (PEKK) and polyetherketone (PEK), carbon fiber reinforced PEEK composites, PEEK-$BaSO_4$ composites, ceramics and composites thereof such as calcium phosphate (e.g. SKELITE™ manufactured by Biologix Inc.), rigid polymers including polyphenylene, polyamide, polyimide, polyetherimide, polyethylene, polyurethanes of any durometer, epoxy and silicone. Different material composites can be used in order to achieve various desired characteristics such as strength, rigidity, elasticity, compliance, biomechanical performance, durability and radiolucency or imaging preference. The matrix used to wrap the reinforcing components of the disclosed pultrusion process may also be fabricated from a heterogeneous material such as a combination of two or more of the above-described materials as long as the resulting material has a melting point that is lower than the melting point of the material used to make the reinforcing fibers.

In assembly, operation and use, implants made from materials produced according to the pultrusion process of the present disclosure may be employed with a surgical procedure for treatment of a spinal disorder affecting a section of a spine of a patient, as discussed herein, for example the implant can be used in areas where increased flexibility is necessary for normal function. That is, in joints, flexion points, intervertebral discs, or used in connection with a surgical procedure to correct spinal fractures, disorders or injury. It is contemplated that implants produced from the disclosed pultrusion process can be used in conjunction with vertebral fusion and/or dynamic stabilization applications of the affected section of the spine so as to facilitate healing and therapeutic treatment, while providing flexion, extension and/or torsion capability. Implants can be coated with osteogenic, or therapeutic materials once produced.

In use, to treat the affected section of the spine, a medical practitioner may obtain access to a surgical site in any appropriate manner, such as through incision and retraction of tissues. It is envisioned that the implant produced in accordance with the pultrusion process of the present disclosure, may be used in any existing surgical method or technique including open surgery, mini-open surgery, minimally invasive surgery and percutaneous surgical implantation, whereby vertebrae V is accessed through a micro-incision, or sleeve that provides a protected passageway to the area. Once access to the surgical site is obtained, the particular surgical procedure is performed for treating the spinal disorder. The implant having increased flexibility can be in the form of a vertebral rod system, plate, bone fastener, or in any other useful structure is then employed to augment the surgical treatment.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A pultrusion process for-preparing a low percent of continuous reinforcing fibers composite material comprising the steps of:

continuously pulling reinforcing fibers through an impregnation chamber comprising a mixture containing precursors and initiators that polymerize when heated above a reaction temperature to produce impregnated continuous reinforcing fibers, wherein the temperature of the impregnation chamber is below the polymerization temperature of the precursors and initiators in the impregnation chamber;

wrapping the continuous reinforcing fibers with strands of curable matrix material having a lower melting point than a melting point of the continuous reinforcing fibers, the continuous reinforcing fibers being selected from the group consisting of metallic wire, carbon fibers, polyolefin fibers, polyester fibers, and aromatic polyamide fibers;

directing the wrapped continuous reinforcing fibers through a heated curing die to melt the matrix material about the wrapped continuous reinforcing fibers and cure the matrix material so as to produce a solid fiber reinforced composite; and withdrawing the solid fiber reinforced composite from the curing die, wherein the percentage of continuous fibers in the solid fiber reinforced composite is between about 10 percent by volume and about 45 percent by volume.

2. A pultrusion process according to claim 1, wherein wrapping the continuous reinforcing fibers comprises wrapping the continuous reinforcing fibers with braided strands of matrix material having a lower melting point than a melting point of the continuous reinforcing fibers.

3. A pultrusion process according to claim 1, wherein the polymer produced from the precursor and initiator is selected from the group consisting of thermoplastic, Nylon, a polyurethane, an epoxy, a polyacrylate, a polymethacrylate, and a thermoset.

4. A pultrusion process according to claim 1, further comprising positioning the wrapped continuous reinforcing fibers in predetermined positions so as to produce a solid fiber reinforced composite having reinforcing fibers positioned in predetermined configurations so as to provide predetermined mechanical properties.

5. A pultrusion process according to claim 1, wherein the percentage of continuous fibers in the solid fiber reinforced composite is between about 15% to about 40% by volume.

6. A pultrusion process according to claim 1, wherein the percentage of continuous fibers in the solid fiber reinforced composite is between about 25% to about 35% by volume.

7. A pultrusion process according to claim 1, wherein the impregnation chamber mixture further comprises at least one additive.

8. A pultrusion process according to claim 7, wherein the additive is a catalytically effective amount of a catalyst selected from the group consisting of organobismuth catalysts and combinations thereof.

9. A pultrusion process according to claim 1, wherein the mixture in the impregnation chamber further comprises short pieces of reinforcement fibers that are configured to contact the continuous reinforcement fibers as it is passed through the impregnation chamber and attach to the continuous reinforcement fibers so as to become trapped between the reinforcing fibers and the wrapped continuous reinforcing fibers so that the solid fiber reinforced composite withdrawn from the curing die contains fragments of reinforcement fibers as well as continuous reinforcement fibers.

10. A pultrusion process according to claim 1, wherein the reinforcing fibers each extend between a first end and a second end and an outer surface of each of the reinforcing fibers is positioned between the first and second ends.

11. A pultrusion process according to claim 1, wherein the strands of the matrix material are wrapped about each of the reinforcing fibers such that at least one of the strands of the matrix material overlaps at least another one of the strands of the matrix material.

12. A pultrusion process according to claim 1, further comprising coating the matrix material with chopped reinforced fibers.

13. A pultrusion process according to claim 1, further comprising coating the matrix material with fragmented reinforced plates.

14. A pultrusion process according to claim 1, further comprising coating the matrix material with particulates of the reinforced fibers.

15. A pultrusion process for-preparing a low percent of continuous reinforcing fibers composite material comprising the steps of:

continuously pulling reinforcing fibers through an impregnation chamber comprising a mixture containing precursors and initiators that polymerize when heated above a reaction temperature to produce impregnated continuous reinforcing fibers, wherein the temperature of the impregnation chamber is below the polymerization temperature of the precursors and initiators in the impregnation chamber;

wrapping the reinforcing fibers with strands of curable matrix material having a lower melting point than a melting point of the continuous reinforcing fibers;

directing the wrapped continuous reinforcing fibers through a heated curing die to melt the matrix material about the reinforcing fibers and cure the matrix material so as to produce a solid fiber reinforced composite; and withdrawing the solid fiber reinforced composite from the curing die wherein the percentage of continuous fibers in the solid fiber reinforced composite is between about 10 percent by volume and about 45 percent by volume.

16. A pultrusion process for-preparing a low percent of continuous reinforcing fibers composite material comprising the steps of:

continuously pulling reinforcing fibers through an impregnation chamber comprising a mixture containing precursors and initiators that polymerize when heated above a reaction temperature to produce impregnated continuous reinforcing fibers, wherein the temperature of the impregnation chamber is below the polymerization temperature of the precursors and initiators in the impregnation chamber;

braiding the continuous reinforcing fibers with strands of curable matrix material having a lower melting point than a melting point of the continuous reinforcing fibers, the continuous reinforcing fibers being selected from the group consisting of metallic wire, carbon fibers, polyolefin fibers, polyester fibers, and aromatic polyamide fibers;

directing the braided continuous reinforcing fibers through a heated curing die to melt the matrix material about the reinforcing fibers and cure the matrix material so as to produce a solid fiber reinforced composite; and withdrawing the solid fiber reinforced composite from the curing die wherein the percentage of continuous fibers in the solid fiber reinforced composite is between about 10 percent by volume and about 45 percent by volume.

17. A pultrusion process according to claim 16, wherein the continuous reinforcing fibers each extend between opposite first and second ends and have an outer surface between the first and second ends, the matrix material covering the outer surface of each of the reinforcing fibers.

18. A pultrusion process according to claim 16, further comprising coating the matrix material with chopped reinforced fibers.

19. A pultrusion process according to claim 16, further comprising coating the matrix material with fragmented reinforced plates.

* * * * *